United States Patent [19]

Kajiwara et al.

[11] Patent Number: 4,978,619
[45] Date of Patent: Dec. 18, 1990

[54] ENZYME IMMOBILIZATION BY ENTRAPMENT IN A POLYMER GEL MATRIX

[75] Inventors: Shigeru Kajiwara, Ibaraki; Hidekatsu Maeda, Nagareyama; Hideo Suzuki, Tokyo, all of Japan

[73] Assignees: Agency of Industrial Science & Technology; Ministry of International Trade & Industry, both of Tokyo, Japan

[21] Appl. No.: 396,762

[22] Filed: Aug. 22, 1989

Related U.S. Application Data

[63] Continuation of Ser. No. 29,952, Mar. 25, 1987, abandoned.

[30] Foreign Application Priority Data

Mar. 25, 1986 [JP] Japan .................................. 61-66156

[51] Int. Cl.$^5$ ...................... C12N 11/08; C12N 11/04
[52] U.S. Cl. .................................... 435/182; 435/180

[58] Field of Search ................ 435/174, 177, 180, 182

[56] References Cited

U.S. PATENT DOCUMENTS

| | | | |
|---|---|---|---|
| 3,859,169 | 1/1975 | O'Driscoll et al. | 435/182 |
| 4,195,127 | 3/1980 | Hartdegen et al. | 435/174 |
| 4,276,381 | 6/1981 | Sakimae et al. | 438/182 X |

Primary Examiner—David M. Naff
Attorney, Agent, or Firm—Oblon, Spivak, McClelland, Maier & Neustadt

[57] ABSTRACT

An immobilized enzyme having an enzyme entrapped in gaps formed in a macromolecular gel matrix is produced by dispersing the enzyme in the form of a fine powder in an organic solvent having dissolved therein a polymerizable monomer, polymerizing the monomer thereby giving rise to a gel matrix, and displacing the organic solvent in the gel matrix with an aqueous solvent.

8 Claims, No Drawings

ENZYME IMMOBILIZATION BY ENTRAPMENT IN A POLYMER GEL MATRIX

This application is a Continuation of application Ser. No. 07/029,952, filed on Mar. 25, 1987, now abandoned.

FIELD OF THE INVENTION AND RELATED ART STATEMENT

This invention relates to an immobilized enzyme and a method for the production thereof.

In various enzymatic reactions, since the enzyme used therein as a catalyst is soluble in water, it can be used only in one batch of the reaction. To overcome this drawback, the technique of using the enzyme as kept in an immobilized state has been developed and has found widespread acceptance.

In recent years, ATP, synthetic enzymes such as NAD and NADP of the class requiring coenzymes, and oxidoreductases besides such hydrolases as amylases and proteases have begun to find utility in the field of medical analysis. They are also nearing adoption as catalysts for the production of medicines and chemicals. Particularly in the case where an optically active substance is produced from a raw material exhibiting no such optical activity at a single stage without bonding any protective radical, almost all of the chemical synthetic methods known to the art fail to produce it. However, use of the aforementioned immobilized enzyme can facilitate the production of the optically active substance. Generally, enzymes which by nature require coenzymes are much more expensive and less stable than the conventional hydrolases or isomerases and, therefore, cannot be immobilized satisfactorily by the conventional method. In the circumstance, the desirability of developing a more efficient method for the immobilization of an enzyme than the conventional method has been desired.

The methods for the immobilization of enzymes are broadly divided into three types. The first method effects the immobilization by physical adsorption of a given enzyme by an ion-exchange resin or activated carbon, for example. This method is simple to operate. It nevertheless has the disadvantage that it is practicable only under limited conditions because the enzyme interacts with the carrier through a relatively weak bond and, therefore, separates from the carrier in the course of continued reaction. The second method effects the immobilization by chemically joining a given enzyme and the carrier with a covalent bond. The separation of the enzyme from the carrier occurs very rarely because the enzyme and the carrier are joined with a strong bond. This method, however, suffers from the disadvantage that the enzyme is liable to be inactivated because the enzyme molecules are chemically modified. This inactivation poses a serious problem particularly when the enzyme to be immobilized happens to be an unstable enzyme such as a dehydrogenase or a monoxygenase. The third method effects the immobilization by entrapping a given enzyme in a gel matrix or microcapsules made such as of acrylamide or K-carrageenan. This entrapping method has an advantage that it entails no inactivation of the enzyme because, unlike the covalent bond method, it does not require the enzyme molecules to be subjected to direct chemical modification. It has another advantage that when the meshes of the gel or the pores of the microcapsule membrane are suitably adjusted in size, the gel or the microcapsules can keep firm hold of the enzyme molecules therein and yet permit selective passage therethrough of small substrate molecules and, consequently, preclude the otherwise possible separation of the enzyme from the carrier. This entrapping method, therefore, can be applied advantageously to the immobilization of an enzyme of the type requiring the aforementioned coenzyme. More often than not, the enzyme of this description forms a dimer or a tetramer. When the formation of a dimer or tetramer has occurred, the component subunits are joined with very weak force. When one subunit of the dimer or tetramer is joined at a certain portion thereof to the carrier through a covalent bond, it is extremely difficult for the dimer or tetramer to be retained intact for a long time. The enzyme of this nature, therefore, can be immobilized advantageously by the entrapping method using a gel. Where two enzymes of different types are to be immobilized together, the method which causes a group of enzymes to be immobilized by being entrapped in microcapsules is the only means available among all the methods heretofore known to the art. Even by the entrapping method using a gel, it is extremely difficult to have two enzymes of different types sealed in each of the segments of the gel. In the case of the method resorting to microcapsulation, the conventional microcapsulation method, though susceptible to only slight leakage of enzyme, has a major disadvantage that when the microcapsules enclosing therein the enzymes are packed in a column and used for continuous production, the microcapsules are deformed to the extent of clogging the interior of the column and aggravating pressure loss.

As a means of entrapping an enzyme for immobilization therefore, the inventors formerly proposed a method which comprises causing liquid drops containing an enzyme to be dispersed in an organic solvent thereby preparing a primary emulsion, dispersing the primary emulsion in an aqueous medium containing a raw material for gel thereby giving rise to a secondary emulsion, subjecting the secondary emulsion to a treatment for conversion of the aforementioned raw material into a gel, and expelling the organic solvent thereby enabling the formed gel to entrap the aforementioned liquid drops (Glossary of Lectures for the 1984 General Meeting of Japan Fermentation Engineering Society).

This method, however, has the disadvantage that the conditions for the preparation of the secondary emulsion are limited and the secondary emulsion can be stabilized only with difficulty.

OBJECT AND SUMMARY OF THE INVENTION

An object of this invention is to provide an entrapping method for the immobilization of an enzyme, which attains the immobilization in a high yield and allows leakage of the enzyme only in a low ratio.

Another object of this invention is to provide an immobilized enzyme which has the enzyme immobilized in the form of live cells or crushed cells without any sacrifice of the activity of the enzyme.

Yet another object of this invention is to provide a method for effectively immobilizing an unstable enzyme or a plurality of enzymes of different types.

To be specific, this invention is directed to a method which comprises dispersing a fine powder containing an enzyme in a solution having a polymerizable monomer or a prepolymer dissolved in an organic solvent, then polymerizing the monomer or prepolymer thereby giving rise to a gel, subsequently displacing the aforementioned organic solvent with an aqueous solvent, and enabling the dispersed and immobilized enzyme to be entrapped with the consequently reticulated gel.

As described above, the enzyme in an activated form is entrapped in the gaps formed in the gel. By optimizing the size of the meshes of the gel destined to form the aforementioned gaps, therefore, the ratio of immobilization of the enzyme is heightened, the ratio of leakage of the enzyme is lowered, the immobilization of a plurality of enzymes of different types is attained with ease, and the enzyme is allowed to come into ample contact and react efficiently with a substrate under treatment.

The other objects and characteristics of the present invention will become apparent from the description given in further detail herein below.

DETAILED DESCRIPTION OF THE PREFERRED EMBODIMENT

The method of this invention for the immobilization of an enzyme comprises dispersing an enzyme or a fine powder containing an enzyme in a solution having a polymerizable monomer or prepolymer dissolved in an organic solvent, polymerizing the monomer or prepolymer as dispersed in the solution thereby giving rise to a gel matrix, then displacing the aforementioned organic solvent with an aqueous solvent, and causing solution of the dispersed and immobilized enzyme thereby causing the dissolved enzyme to be entrapped in gaps to be formed in the consequently reticulated macromolecular gel matrix.

The enzyme to be subjected to immobilization by the method of this invention need only meet the requirement that it should remain in a solid state during the course of treatment for immobilization. Any enzyme can be used unless it is particularly unstable. Concrete examples of the enzyme usable effectively for the immobilization are enzymes of the class requiring various coenzymes including dehydrogenases such as alcohol dehydrogenases, aldehyde dehydrogenases, glutamic acid dehydrogenase, isoleucine dehydrogenase, formic acid dehydrogenase, malic acid dehydrogenase, glucose-6-phosphoric acid dehydrogenase, and glyceraldehyde-3-phosphoric acid dehydrogenase; monooxygenases such as orcinol-2-monooxygenase and phenol-2-monooxygenase; and kinases such as acetic acid kinase, hexanase, and glycerol kinase; hydrogenases such as $\beta$-amylase, glucoamylase, $\beta$-glucosidase, lipase, phosphatase, protease, and esterases; and oxygenases such as glucose oxidase and peroxidase. These enzymes can be used in a refined form or in a crude form. They may be used, therefore, as contained in dried culture broth, dried culture filtrate, live microorganic cells, dried microorganic cells, crushed microorganic cells, animal and plant cells, crushed cells, and organellas which invariably possess high enzymatic activity. At the time of immobilization, all these materials are required to be in the form of a finely divided powder having a particle size in the range of several $\mu$m to some hundreds of $\mu$m. The smaller the particle size of the enzyme powder, the easier the uniform dispersion of the enzyme powder. However, since enzymes are liable to lose their enzymatic activity when receiving mechanical impacts, the particle size of the enzyme powder should be determined by taking the enzyme stability into consideration. These enzymes can be used either independently of one another or as suitably combined in the form of a mixture. Enzymes of the type which induce a coupled reaction through the medium of a coenzyme prove to be particularly desirable raw materials for the present invention. In the present invention, since the enzyme, though confined in fixed gaps, remains in a free state, the reaction thereof does not experience the physical or steric hindrance observed as in the covalent bond immobilization. Further, since the enzyme is present in a concentrated state in the limited spaces, called gaps herein, within the macromolecular gel, the coupled reaction proceeds quickly to give rise to a highly desirable immobilized enzyme. Since the enzyme is confined within the macromolecular gel, it does not offer sufficient activity when the enzyme happens to be of a type suitable only for a macromolecular substrate or to be a hydrogenase such as $\alpha$-amylase, chitinase, or cellulase. The enzyme, however, manifests ample activity in the hydrolysis of a low-molecular substrate.

The immobilization of an enzyme according to this invention is initiated by mixing an enzyme or a fine powder containing an enzyme (hereinafter referred to simply as "enzyme powder") with a solution obtained by dissolving a polymerizable monomer or prepolymer in an organic solvent thereby preparing an emulsion having the enzyme powder dispensed in the organic solvent solution of the polymerizable monomer or prepolymer. In this case, the enzyme powder may contain an adjuvant of common use such as, for example, a stabilizer in addition to a stabilizer. As concerns the preparation of the aforementioned emulsion, a surfactant may be added in advance to the organic solvent solution of the polymerizable monomer or prepolymer for the purpose of promoting the dispersion of the enzyme powder in the solution.

The aforementioned stabilizer to be contained in the enzyme powder is a chemical agent capable of stabilizing the enzyme. Any of various chemical agents of this description heretofore known to the art can be used. Examples of the stabilizer usable for this purpose include proteins such as hemoglobin, gelatin, and blood serum albumin; polysaccharides such as gum arabic, starch, dextrin, lactose, maltose, and glucose; water-soluble synthetic high polymers such as polyethylene glycol and polyvinyl alcohol; coenzymes such as NAD, NADP, and ATP; chelating agents such as EDTA; and various metal salts and antioxidants such as glutathione which are intended for use in special cases. They are selected to suit the enzyme in use. Generally, commercially available enzyme preparations contain such stabilizers which are intended to enable the preparations to retain their enzymatic activity intact for a long time. When the enzyme to be used inherently possesses high stability, the addition of such a stabilizer as described above is not found necessary. When a stabilizer of a low molecular weight is used, it is not desired to be of a type which is liable to hinder gelation (cross-linking reaction) of a macromolecular substance.

The polymerizable monomer or prepolymer to be dissolved in the organic solvent serving as a dispersant for the enzyme powder must be soluble in the organic solvent and capable of undergoing gelation in the organic solvent being used. It must fulfill a requirement that it should avoid interfering with the displacement of the organic solvent with water. Concrete examples of such monomer or prepolymer include such soluble monomers and prepolymers capable of addition polymerization as vinyl esters, vinyl ethers, acrylic esters, methacrylic esters, acrylamide, and acrylonitrile. Further, monomers which are soluble in organic solvents and have solubility variable with the pH are also usable.

Examples of monomers which are soluble in alkalis and not soluble in acids include crotonic acid, maleic acid, itaconic acid, citraconic acid, and vinyl benzoic acid monomers besides acrylic acid monomer and methacrylic acid monomer, monomers combining vinyl monomer and acid radicals, cellulose derivatives, phthalic acid, succinic acid, and maleic acid derivatives of starch, and phthalic acid derivatives of cellulose. Examples of basic monomers which are soluble in acids and not soluble in alkalis include vinyl pyridine, vinyl imidazole, vinyl amine, and vinyl aniline.

Besides, such compounds as polyvinyl alcohols, polyethylene imines, polyacrylamides, and polyvinyl pyrrolidone which are macromolecules and yet are capable of forming a gel through a cross-linking agent are usable. In the present invention, such macromolecules capable of forming a gel are treated as prepolymers.

The organic solvent to be used as a dispersant for the enzyme powder has only to avoid containing any significant amount of water and to be soluble, if slightly, in water. Examples of the organic solvent meeting this description include acetone, methanol, ethanol, ethylene glycol, formamide, dimethylsulfoxide, methyl cellosolve, N,N-dimethylformamide, dioxane, benzene, cyclohexane, ethyl ether, ethyl acetate, chloroform, and halogenated ethylenes. These organic solvents may be used either independently of one another or as suitably combined in a mixture.

Then, to the emulsion prepared as described above, a polymerization initiator or other similar agent is added so as to induce gelation (cross-linking reaction) of the polymerizable monomer or prepolymer present in the emulsion. In this case, the gelation of the polymerizable monomer or prepolymer is effected by using a method of gelation which particularly suits the polymerizable monomer or prepolymer. This method can be selected from among the various methods heretofore known to the art.

In the present invention, the treatment of gelation is carried out to effect gelation of the polymerizable monomer or prepolymer contained in the organic solvent as the dispersant after the dispersion of the enzyme powder is completed as described above. The method to be used for the gelation in this case is selected so as to suit the monomer or prepolymer being gelled. Concrete examples of the method of gelation will be cited below as associated each with a macromolecular substance to be used therein. For a synthetic prepolymer such as polyethylene glycol diacrylate which possesses a vinyl group, the cross-linking method which effects radical polymerization of the vinyl group of the prepolymer is used; for a polyvinyl alcohol, the cross-linking method resorting to glutaraldehyde or epichlorohydrin, the cross-linking method relying on radiation, or the optical cross-linking method involving irradiation of ultraviolet light in the presence of sodium benzoate is used; for polyethylene imine, the cross-linking method relying on epichlorohydrin is used; and for a polyacrylamide or polyvinyl pyrrolidone, the cross-linking method resorting to radiation is used.

In the production of an immobilized enzyme in accordance with this invention, the amount of the polymerizable monomer or prepolymer to be contained in the organic solvent being used as the dispersant for the enzyme powder is in the range of 0.5 to 30% by weight. If the amount is less than 0.5% by weight, it is impossible to obtain a gel having sufficiently high mechanical strength. If it is more than 30% by weight, then the meshes of a gel matrix being formed become so small that an immobilized enzyme to be produced cannot exhibit sufficiently high enzymatic activity because dispersion of a substrate or copolymers is prevented. The weight ratio of the enzyme powder to the organic solvent solution containing the polymerizable monomer or prepolymer and used for the dispersion of the enzyme powder is in the range of 1:5 to 1:20. If the weight ratio falls short of the range, the mechanical strength of the gel is lowered. If it exceeds the range, the mechanical strength of the gel is enhanced while the amount of the enzyme sealed is decreased, thereby lowering the enzymatic activity.

The macromolecular gel obtained as described above and destined to disperse and retain is finely divided to a particle diameter suitable for packing in a column (about 0.01 to 5 mm, for example), and washed with a large amount of an aqueous solvent such as a buffer so as to effect displacement of the organic solvent in the gel with the aqueous solvent. In this case, the aqueous solvent may be intimately admixed with a solvent such as ethanol which is miscible with water so as to promote the displacement. A typical example of aqueous solvent is water. However, salt solutions such as phosphate, acetate, citrate buffer solutions, a Good buffer solution, a physiological saline solution, etc. suitable for the enzyme to be immobilized can also be used instead. Owing to the change of the solvent in the gel from the organic solvent to the aqueous solvent, the enzyme powder so far dispersed and immobilized in the organic solvent is dissolved in the gaps distributed in the gel matrix, to give rise to an active immobilized enzyme. The gaps in which the enzyme powder has existed or the enzyme powder already in a dissolved state exists have sizes of several $\mu$m to some hundreds of $\mu$m, depending on the particle size of the dispersed enzyme powder.

This invention, as described above, effects the immobilization of the enzyme powder by causing the enzyme powder to be dispersed and retained in the macromolecular gel matrix and subsequently carrying out the displacement of the solvent thereby dissolving and activating the theretofore solid enzyme. The organic solvent has been selected as the solvent for the reaction of gelation on the theory that the prepolymer or the polymer resulting from polymerization of the monomer is cross-linked more advantageously without any alteration of the linear structure of the macromolecular chain in the organic solvent than in an aqueous solvent. As regards the reaction of gelation, whereas the conventional gel entrapping method represses leakage of the enzyme only with difficulty because the gelation is carried out in the aqueous solvent, the method of the present invention is capable of adjusting the meshes of the gel uniformly over a wide range by suitable selection of the reaction conditions and, therefore, optimizing the gel meshes with respect to the particular enzyme selected to be immobilized. Further, since the enzyme exists as a solid away from the reaction solution in the polymerization reaction so as not to lose its activity and since the enzyme molecules and enzyme stabilizers are separated from the reaction solution, the polymerization reaction proceeds without being adversely affected to produce gel meshes of a uniform size. Therefore, this method is characterized by the fact that the ratio of immobilization of an enzyme is high and the ratio of leakage of the enzyme is extremely low. In accordance with the present invention, the enzyme can be subjected to the immobilization as contained in the crushed microorganic cells, dried microorganic cells, or live microorganic cells. Moreover, the method is capable of effectively immobilizing an unstable enzyme or a plurality of enzymes of different types such as, for example, a plurality of enzymes of the type inducing a coupled reaction.

Now, the present invention will be more specifically described below with reference to working examples.

EXAMPLE 1

In a test tube, 2.5 units of a freeze-dried formic acid dehydrogenase (a product of Behringer GmbH marketed under trademark "Formic Acid Dehydrogenase"; hereinafter referred to as "FDH" for short) was comminuted with a glass rod. The enzyme powder thus prepared and 2 ml of chloroform containing 400 mg of polyethylene glycol (#400) diacrylate (hereinafter referred to as "PEGDA #400" for short) deaerated in advance for 20 minutes were stirred under a current of nitrogen for dispersion of the enzyme powder. After the enzyme powder as thoroughly dispersed, 5 mg of a polymerization initiator (benzoyl peroxide) and 5 $\mu$l of a polymerization accelerator (dimethyl aniline) were added to the dispersion in the test tube to induce polymerization. In about 1 minute's time, the suspension began to form gel. Then, the suspension in the process of polymerization was left standing at room temperature for 30 minutes for completion of the polymerization. The gel consequently formed was coarsely crushed and left standing in 50 ml of chloroform for 30 minutes for expulsion of the unaltered portions of the polymerization initiator and polymerization accelerator. The coarsely crushed gel was suction filtered for removal of chloroform. It was then placed in a 0.1M tris-hydrochloride buffer (pH 7.5) and chopped with a cutter into cubes of about 0.2 mm. The gel cubes were washed by stirring in 1 liter of a 0.1M trishydrochloride buffer (pH 7.5) overnight to effect displacement of the chloroform solvent contained in the gel with the buffer. The washings were removed by suction filtration, to obtain an immobilized enzyme (1.3 g).

Then, the residue of the suction filtration was tested for unimmobilized FDH activity and the gel washings were tested for unimmobilized FDH activity and for immobilized FDH activity as follows. The term "1 unit (u)" of FDH as used herein means the activity of the enzyme which is required in 1 mol of formic acid at pH 7.5 and 30° C. in one minute.

In the test for unimmobilized FDH activity, the FDH activity was determined by using a 0.1M phosphate buffer (pH 7.5) containing 33 mM of formic acid and 1 mM of NADH and finding the initial velocity of increase in the absorbance of 340 nm at 30° C. The immobilized FDH activity was also determined under the same conditions as described above.

As a result, the washings of gel were found to contain 5.5% of the total FDH activity in the initial feed, indicating that the enzyme activity was immobilized with very high efficiency. The total enzymatic activity of the immobilized enzyme was found to be 14% of the FDH activity expected to be immobilized (the difference between the FDH activity in the initial feed and the FDH activity in the washings). This apparent decline of activity is thought to have originated in the resistance to the inner dispersion of gel.

EXAMPLE 2

FDH was dissolved in distilled water and the resulting aqueous FDH was saturated to 80% with ammonium sulfate by the addition of a saturated aqueous solution of ammonium sulfate to induce precipitation of FDH. The mixture consequently formed was centrifuged (15,000 rpm, 4° C., 3 minutes) to recover a precipitate. The ammonium sulfate precipitate was stripped of the water component thereof by addition of cold acetone and then centrifuged to obtain an acetone-treated FDH. Separately, the ammonium sulfate precipitate was dispersed in hexane containing an extremely small amount of a surfactant (a product marketed under trademark "Span 80"). The resulting dispersion was centrifuged (15,000 rpm, 4° C., 3 minutes) for expulsion of hexane. The resulting precipitate was stripped of the residual water component thereof by addition of cold acetone and centrifuged (15,000 rpm, 4° C., 3 minutes) for expulsion of acetone. Consequently, a hexane-acetone-treated FDH was obtained Then, 1.68 units of the aforementioned acetone-treated FDH and 1.05 units of the hexane-acetone-treated FDH were severally dispersed in 1 ml of benzene. Separately, 1 ml of benzene containing 400 mg of PEGDA #400 was prepared. These benzene dispersions were each deaerated for 20 minutes. The two benzene dispersions of FDH were separately combined with the benzene dispersion of PEGDA #400 and subjected to deaeration for 10 minutes. To the benzene dispersions of the different enzymes, polymerizing by addition of 5 mg of a polymerization initiator (benzoyl peroxide) and 5 $\mu$l of a polymerization accelerator (dimethyl aniline) were added under a current of nitrogen to induce polymerization. Under the conditions, polymerization began to occur in about 30 minutes. The dispersions were left standing at room temperature for one hour to complete the polymerization. The gel consequently formed was coarsely crushed and immersed in 50 ml of benzene to expel the unaltered portions of the polymerization initiator and the polymerization accelerator. One hour after this treatment, the coarse grains of gel thus treated were suction filtered for removal of benzene. Then, they were chopped in a 0.1M tris-hydrochloride buffer (pH 7.5) into cubes of about 0.2 mm with a cutter. The gel cubes were washed by stirring overnight in 250 ml of a 0.1M tris-hydrochloride buffer (pH 7.5) to effect displacement of the benzene solvent in the gel with the buffer. The gel thus treated was suction filtered for removal of the washings. Consequently, an immobilized enzyme (1.1 g) was obtained.

Then, the washings of the gel were tested for FDH activity and for immobilized FDH activity by following the procedure of Example 1. As a result, the washings were found to contain 11% of the total FDH activity in the initial feed in the case of the acetone-treated FDH and 26% of the total FDH activity in the case of the hexane- acetone-treated FDH respectively. The total enzyme activity of the immobilized FDH was 18% of the FDH activity expected to be immobilized in the case of the acetone-treated FDH and 25% in the case of the hexane-acetone-treated FDH, respectively. Thus, immobilized FDH's of high enzymatic activity were obtained Either of these immobilized FDH's taken in 1 g, was dispersed in 25 ml of a 0.1M tris-hydrochloride buffer (pH 7.5) and shaken to be washed again at room temperature. After this shaking had been continued for two days, the dispersion was suction filtered for removal of the washings.

The washings and the immobilized FDH were tested for activity. As a result, the washings were found to contain no FDH activity in the case of the acetone-treated FDH and to contain only 0.15% of the FDH activity in the initial feed in the case of the hexane-acetone-treated FDH. These results indicate that the immobilized enzymes thus obtained suffered substantially no leakage of enzyme from the gel. It is presumed that the heavy loss of the enzymatic activity during the first washing was due to the direct leakage of the enzyme from the enzyme packets of the gel exposed when the gel was chopped. The ratio of enzyme immobilization could be improved as by correcting the arrangement of particles of the gel. In either case, the activity of the immobilized FDH was completely identical with the activity acquired at the time of immobilization.

EXAMPLE 3

Freeze-dried FDH, 2.5 units, was comminuted and dispersed in 2 ml of dimethyl sulfoxide containing 360 mg of acrylamide and N,N-methylenebisacrylamide. The resulting dispersion was deaerated for 30 minutes To the deaerated dispersion, 5 mg of a polymerization initiator (benzoyl peroxide) and 5 μl of a polymerization accelerator (dimethyl aniline) were added under a current of nitrogen to induce polymerization. In about 1 minute, gelation began to occur. This dispersion was left standing at room temperature for one hour to complete the polymerization. The gel consequently formed was chopped into cubes of about 0.2 mm with a cutter and washed by stirring overnight in 1 liter of a 0.1M tris-hydrochloride buffer (pH 7.5) to effect displacement of the solvent in the gel. The washed gel cubes were suction filtered for removal of the washings. Consequently, an immobilized enzyme (3.3 g) was obtained.

Then, the washings of gel were tested for FDH ractivity and for immobilized FDH activity by following the procedure of Example 1. As a result, no activity was detected in the washings of gel. The total enzymatic activity of the immobilized FDH was 9.6% of the activity expected to be immobilized. Even by the use of the combination of acrylamide and methylenebisacrylamide, there could be obtained an immobilized enzyme possessing the same activity as PEGDA.

In 1 liter of a 0.1M tris-hydrochloride buffer (pH 7.5), 3 g of this immobilized enzyme was washed by stirring for five days. The washed immobilized enzyme was suction filtered for removal of the washings. The washings and the immobilized FDH were tested for activity. As a result, no FDH activity was detected in the washings, indicating that the immobilized enzyme consequently obtained suffered substantially no leakage of enzyme. The activity of the immobilized FDH was substantially the same as that acquired at the time of preparation. Thus, the immobilized enzyme produced herein possessed high stability.

EXAMPLE 4

Freeze-dried FDH, 2.6 units, was comminuted and dispersed in 2 ml of chloroform containing 400 mg of polyethylene glycol (#1000) dimethacrylate. The resulting dispersion was deaerated for 20 minutes. To the deaerated dispersion, 5 mg of a polymerization initiator (benzoyl peroxide) and 5 μl of a polymerization accelerator (dimethyl aniline) were added under a current of nitrogen to induce polymerization. In about 6 minutes, gelation began to occur. This dispersion was left standing at room temperature for 30 minutes to complete the poyymerization. The gel consequently formed was coarsely crushed and left standing in 50 ml of chloroform for one hour for expulsion of the unaltered portion of the polymerization initiator and the polymerization accelerator. The gel powder was suction filtered for removal of chloroform and then comminuted with a waring blender. The comminuted gel was washed by stirring overnight in 1 liter of a 0.1M tris-hydrochloride buffer (pH 7.5) to effect displacement of the solvent in the gel. The washed gel was suction filtered for removal of the washings. Consequently, an immobilized enzyme (1.4 g) was obtained.

Then, the washings of gel were tested for FDH activity and for immobilized FDH activity. As a result, 7.5% of the FDH activity in the initial feed was detected in the washings of gel. The total enzymatic activity of the immobilized FDH was 10.5% of the activity expected to be immobilized. Thus, even by the use of the monomer mentioned above, the immobilized enzyme having the same activity as that of PEGDA could be obtained.

Then, in 100 ml of a 0.1M tris-hydrochloride buffer (pH 7.5), 1 g of the immobilized enzyme was washed by stirring for five days. The washed immobilized enzyme was suction filtered for removal of the washings. The washings and the immobilized FDH were tested for activity. As a result, the washings were found to contain 0.8% of the FDH activity in the initial feed, indicating that the immobilized enzyme thus produced suffered only slight leak of enzyme. The immobilized FDH showed substantially the same activity as that acquired at the time of preparation. Thus, the immobilized enzyme enjoyed high stability.

EXAMPLE 5

An ammonium sulfate precipitate of an alcohol dehydrogenase (a product of Behringer GmbH, originating in the horse liver and marketed under trademark "Alcohol Dehydrogenase"; hereinafter referred to as "ADH" for short) was centrifuged (15,000 rpm, 4 minutes). The residue of the centrifugation was deprived of the water component by addition of cold acetone and again centrifuged (15,000 rpm, 4 minutes). The residue of the second centrifugation was vacuum dried, to produce ADH powder.

Two portions, 2.5 units each, of the ADH powder were dispersed separately in 2 ml of chloroform respectively containing 400 mg of polyethylene glycol (#400) diacrylate (hereinafter referred to as "PEGDA #400" for short) and 400 mg of polyethylene glycol (#600) dimethacrylate (hereinafter referred to as "PEGDMA #600" for short). The resulting dispersions were deaerated for 30 minutes. To the deaerated dispersions, 5 mg of a polymerization initiator (benzoyl peroxide) and 5 μl of a polymerization accelerator (dimethyl aniline) were added under a current of nitrogen to induce polymerization. In either case, gelation began to occur in about 6 to 7 minutes. These dispersions were left standing at room temperature for 30 minutes to complete the polymerization. The gels consequently formed were coarsely crushed and left standing in 50 ml of chloroform for 30 minutes for expulsion of the unaltered portions. The coarse gel powders were suction filtered for removal of chloroform, then comminuted with a whirling blender, and washed by stirring overnight in 1 liter of a 0.1M tris-hydrochlorie buffer (pH 7.5) to effect displacement of the solvent in the gel. The gels so treated were suction filtered for removal of the washings. Consequently, there were obtained 1.1 g of immobilized enzyme (PEGDA #400) and 1.0 g of immobilized enzyme (PEGDMA #600).

Then, the unimmobilized ADH and the ADH activity and the immobilized ADH activity in the washings were determined as follows.

The term "1 unit of ADH" as used herein means the enzymatic activity which is required in oxidizing 1 μ.mol of ethanol at pH 9.0 at 30° C. for one minute.

In the test for unimmobilized ADH, the ADH activity was determined by using a 62.1 mM glycin-sodium pyrophosphate buffer (pH 9.0) containing 577 mM of ethanol, 1.8 mM of NAD, 10 mM of reduced glutathin, and 72.8 mM of semicarbazide and finding the initial velocity of the increase in the absorbance of 340 nm at 30° C.

As a result, 5.4% of the ADH activity in the initial feed was detected in the washings from the immobilization of PEGDA #400. No ADH activity was detected in the washings from the immobilization of PEGDMA #600. Thus, the enzyme activity was immobilized with very high efficiency. The total enzymatic activity of the immobilized ADH was 20% of the ADH activity expected to be immobilized (in the case of PEGDA #400) and it was 15% (in the case of PEGDMA #600). These results indicate that the method of the present invention can be applied effectively to other dehydrogenases than FDH.

EXAMPLE 6

Ammonium sulfate precipitates of a hexokinase (a product of Behringer GmbH, originating in yeast and marketed under trademark "Hexokinase"; hereinafter referred to as "HK" for short) and a glucose-6-phosphoric acid dehydrogenase (a product of Behringer GmbH, originating in yeast and marketed under trademark "Glucose-6-phosphoric acid Dehydrogenase"; hereinafter referred to as "G6PDH" for short) were centrifuged (15,000 rpm, 4 minutes). The residues of the centrifugation were stripped of the water component by addition of cold acetone and again centrifuged (15,000 rpm, 4 minutes). The residues of the second centrifugation were dried to produce enzyme powders. The HK powder, 8.0 units, and the G6PDH powder, 9.3 units, were separately dispersed in 2 ml of chloroform containing 400 mg of polyethylene glycol (#400) diacrylate. The dispersions were deaerated for 30 minutes. To the deaerated dispersions, 5 mg of a polymerization initiator (benzoyl peroxide) and 5 μl of a polymerization accelerator (dimethyl aniline) were added to induce polymerization. In about 1 minute, gelation began to occur. These dispersions were left standing at room temperature for 30 minutes to complete the polymerization. The gels consequently formed were coarsely crushed and left standing in 50 ml of chloroform for two hours for removal of the unaltered portions. The coarse gel powders were suction filtered for removal of chloroform and then comminuted with a waring blender and then washed by stirring overnight in 1 liter of 0.1M phosphate buffer (pH 7.0) to effect displacement of the solvent in the gel. The gels so treated were suction filtered for expulsion of the washings. Consequently, there was obtained an immobilized enzyme (960 mg).

Then, the unimmobilized G6PDH and HK, the unimmobilized G6PDH and HK in the washings of gel, and the immobilized G6PDH and HK were tested for activity as follows.

The term "1 unit (u) of G6PDH" as used herein means the enzymatic activity which is required in oxidizing 1 μ.mol of glucose-6-phosphoric acid at pH 7.6 at 30° C. in one minute. Then, the term "1 unit (u) of HK" as used herein means the enzymatic activity which is required in phosphorylating 1 μ.mol of glucose at pH 7.6 at 30° C. in one minute. The product of HK was glucose-6-phosphoric acid and the amount of glucose-6-phosphoric acid was determined as reduced to the amount of NADH in the presence of G6PDH in excess.

In the test of the unimmobilized G6PDH for activity, the G6PDH activity was determined by using a 86.3 mM triethanolamine buffer (pH 7.6) containing 1.2 mM of glucose-6-phosphoric acid, 0.37 mM of NADP, and 6.7 mM of magnesium chloride and finding the initial velocity of the increase in the absorbance of 340 nm at 30° C. The activity of immobilized G6PDH was determined by the same method as described above. In the test of HK for activity, the HK activity was determined by using a 82.3 mM triethanol amine buffer (pH 7.6) containing 222 mM of glucose, 2.7 mM of ATP (adenosine-5-triphosphoric acid), 0.73 of NADP (nicotin-adenine-dinucleotide-phosphoric acid), 6.7 mM of magnesium chloride, and 0.5 μ of G6PDH per ml and finding the initial velocity of the increase in the absorbance of 340 nm at 30° C. The activity of the immobilized HK was determined by using the same method as described above.

The coupled reaction of HK and G6PDH was studied by using the substrate solution for the determination of HK activity minus G6PDH and finding the formation of NADPH solely by the immobilized enzyme at 30° C., namely, the increase in the absorbance of 340 nm.

As a result, in the immobilized enzyme, 8.2% of the HK activity expected to be immobilized and 12.7% of the G6PDH activity expected to be immobilized were detected. When the coupled reaction of the immobilized HK activity and G6PDH activity was studied, it was confirmed to possess a coupled activity equivalent to the HK activity of the immobilized enzyme. It was consequently confirmed that the amount of glucose could be determined by this immobilized enzyme.

EXAMPLE 7

In a Sakaguchi flask having an inner volume of 500 ml, 50 ml of a fermentation broth (pH 7.0) containing 0.1% of potassium dihydrogen phosphate, 0.05% of magnesium sulfate heptahydrate, 0.01% of calcium chloride dihydrate, 0.02% of sodium chloride, 0.4% of casamino acid, 0.1% of yeast extract, and 8% of D-xylose were sterilized with an autoclave (120° C., 20 minutes). In the sterilized broth, Pichia xylosa (IFO 0950) inoculated thereto was subjected to agitation culture at 30° C. for 3 days. The resulting culture broth was centrifuged (8,000 rpm, 10 minutes). The residue of the centrifugation was washed three times with a 0.05M phosphate buffer (pH 7.0) to produce 2.7 g of washed cells.

In 1 ml of benzene, 20 mg of the washed cells were dispersed in the presence of four drops of a surfactant (Span 85). One (1) ml of benzene containing 400 g of PEGDA #400 and the cell dispersion obtained as described above were separately deaerated for 20 minutes. The two deaerated liquids were combined and again deaerated for 20 minutes. To the deaerated mixture, 5 mg of benzoyl peroxide and 5 μl of dimethyl aniline were added under a current of nitrogen to induce polymerization. In about 4 minutes, gelation began to occur. This mixture was left standing for 30 minutes to complete the gelation. The gel consequently formed was crushed into cubes of 5 mm. The gel cubes were washed with 50 ml of benzene to expel the unaltered portions of the reagents used. The gel was stripped of benzene and then washed with 300 ml of a 0.05M phosphate buffer (pH 7.0) for two hours. The washed gel was suction filtered for removal of the washings. Consequently, immobilized cells (0.8 g) were obtained. These immobilized cells were transferred into 10 ml of the aforementioned cultured broth and subjected to shaken culture at 30° C. for four days. The culture broth containing the gel was filtered to separate out the broth. A segment was cut from the gel and observed under a microscope. Consequently, growth of microorganic cells in the gel was recognized. When the culture broth was analyzed for sugar content by high performance liquid chromatography, consumption of D-xylose and formation of xylitol were recognized. The analysis for sugar content by the high performance liquid chromatography was carried out by keeping an ion-exchange column (a product of Showa Denko K. K. and marketed under trademark "Shodex C-811") at 80° C., using water as a solvent, and feeding the sample at a rate of 1.0 ml/minute. A differential refractometer (a product of Showa Denko K. K. marketed under trademark "Shodex SE-11") was used as a detector and the output of the detector was processed with a chromatograph data processing device (a product of Shimadzu Corp. Ltd. marketed under trademark "Chromatopack CR3-A") to find the areas of the peaks. The concentrations of the different substances involved were determined by comparing these areas with the peak areas of the standard samples of known concentrations.

EXAMPLE 8

Freeze dried microorganic cells (0.5 g of dried microorganic cells/2.7 g of wet live microorganic cells) were obtained by freeze drying the same live microorganic cells as used in Example 7. In 1 ml of benzene, 20 mg of the freeze dried microorganic cells were dispersed. This dispersion and 1 ml of benzene containing 400 g of PEGDA #400 were severally deaerated for 20 minutes. The two liquids were combined and deaerated for 20 minutes. To the deaerated mixture, 5 mg of benzoyl peroxide and 5 $\mu$l of dimethyl aniline were added under a current of nitrogen to induce polymerization. In about 3 minutes, gelation began to occur. This mixture was left standing at room temperature for 30 minutes to complete the gelation. The gel was coarsely crushed and washed with 50 ml of benzene for 30 minutes. The washed gel was stripped of benzene, comminuted with a waring blender, and washed by stirring overnight in 350 ml of a 0.05M phosphate buffer (pH 7.0) to effect displacement of the solvent. The gel thus treated was suction filtered for expulsion of the washings. Consequently, immobilized dry microorganic cells (1.0 g) were obtained.

In 1 ml of a 0.05M phosphate buffer (pH 7.0) ontaining 20 mM of NADP, 0.5M of glucose, 0.3M glucose-6-phosphoric acid, and 3.5 units of G6PDH, 200 mg of the immobilized dry microorganic cells were placed and subjected to reciprocation at 30° C. for 24 hours to induce reaction. The resulting reaction solution was analyzed for sugar content by the same high performance liquid chromatography as described in Example 7. It was consequently confirmed that the glucose in the reaction solution was converted to sorbitol. The activity of the reaction solution was 5% of the conversion activity of the freeze dried microorganic cells of the initial feed.

EXAMPLE 9

An enzyme solution containing 80 units of leucine dehydrogenase (a product of Toyodo Co., Ltd., Japan, originating in Bacillus sp and marketed under trade name "leucine dehydrogenase"; hereinafter referred to as "LeuDH"), 15 units of FDH, 450 mg of dextrin, 50 mg of Bovine serium albumin, 1.2 mg of cystein, 1.1 mg of dithiothreitol, 0.6 $\mu$l of 2-mercaptoethanol and 2.6 mg of EDTA in 5 ml of 0.1M phosphate buffer (pH 7.5) was freeze-dried for 20 hours. The enzyme solid was ground into fine powder using a mortar and a pestle and 510 mg of enzyme powder was obtained. A monomer solution containing 320 mg of PEGDA #4000, 40 mg of N,N'-methylenebisacrylamide and 40 mg of 2-hydroxyethylacrylate in 1.97 ml of methylcellosolve saturated with nitrogen gas, was added to 200 mg of the enzyme powder having 26.6 units of LeuDH activity and 4.95 units of FDH activity in a sealed bottle. After degassation by an aspirator for 5 min with continuous stirring, 20 $\mu$ of methylcellosolve containing 1.0 mg of benzoylperoxide and 10 $\mu$l of methylcellosolve containing 1.0 $\mu$l of N, N-dimethylaniline were added to the mixture in order and the mixture was kept at 35° C. in a nitrogen atmosphere. A gel was formed within 35 to 40 min, and the gellation was further allowed to proceed for 5 hours at 35° C. The gel was cut with a cutter and the particles were washed in 1,000 ml of 0.1M phosphate buffer (pH 7.5) with continuous stirring for one night to remove methylcellosolve and dextrin from the enzyme powder. After washing, the immobilized LeuDH-FDH gel was collected on a buchner funnel.

The term "1 unit (u) of LeuDH" as used herein means the enzymatic activity which is required in reducing 1 $\mu$.mol of $\alpha$-ketoisocaproic acid at pH 7.5 at 30° C. in one minute.

The free and immobilized enzymes were assayed at 30° C. by measuring the absorbance change at 340 nm due to the oxidation of NADH by LeuDH in thermostatted cells. The following substrate solutions were used for both free and immobilzed enzymes: 10.0 mM sodium $\alpha$-ketoisocaproate and 0.1 mM of NADH in 0.75M ammonia chloride - NaOH buffer (pH 7.5) in a total volume of 3.00 ml.

The total wet weight of the gel was 2.33 g. The LeuDH and FDH activities of the washing solution were 17.5% and 27.2% of the added activities, respectively. The LeuDH and FDH activities of the gel were 0.37 units/g wet and 0.28 units/g wet, respectively. The expressed LeuDH and FDH activities of the gel were 4.0% and 18.3% of the initial activities, respectively. The activities of the gel were dependent on the substrate concentration, especially NADH concentration. Therefore, the low expressed LeuDH activity is due to low NADH concentration in the assay condition.

Continuous leucine production was carried out for 4 weeks using the column packed with LeuDH-FDH gel. The substrate solution was composed of 10 mM of sodium $\alpha$-ketoisocaproate, 100 mM of sodium formate, 20 mM of ammonium chloride, and 0.3 mM of NAD, with 0.1 mM of 2-mercaptoethanol and 0.1 mM of EDTA as stabilizers, and with 0.01% of potassium sorbate as a preservative in 0.05 M Tris-HCl buffer (pH 7.5). Five hundred milligrams of the gel was packed in a column (5 mm i.d. $\times$ 70 mm long) and the substrate solution was passed downward through the column at a flow rate of 15.0±0.5 ml/hr. The temperature of the column was kept at 30° C. and the other parts of the reactor were maintained at 4° C. The substrate solution was also kept at 4° C. and replaced with a freshly prepared one every day. The effluent was collected by a fraction collector and the amount of leucine in each fraction was determined by amino acid analysis system.

The conversion ratio gradually decreased up to the tenth day at the rate of 0.8%/day. There was almost no decrease of activity after the tenth day. The LeuDH-FDH gel column maintained about 90% productivity compared with the initial level, even after 28 days. The LeuDH and FDH activities of the LeuDH-FDH gel remaining in the column after 28 days' operation were 92% and 90% of the initial activities, respectively. Since the reaction of FDH is the rate limiting step of the coupled enzyme reaction, the decrease in leucine productivity is considered to reflect the decrease of FDH activity in the LeuDH-FDH gel. The expressed activity of FDH calculated from the leucine production rate was 23% of the entrapped FDH activity in the gel at the starting point.

EXAMPLE 10

Two hundred milligrams of the enzyme powder having 64.1 units of LeuDH activity and 35.2 units of FDH activity was immobilized according to Example 9. After cutting the gel and washing for one night, the total wet weight of the immobilized LeuDH-FDH gel was 2.13 g. The added total LeuDH and FDH activities of the washing solution were 19.4% and 23.3%, respectively. The LeuDH and FDH activities of the gel were 0.60 units/g wet and 1.0 units/g wet, respectively.

The substrate solution was composed of 100 mM of sodium α-ketoisocaproate, 1 mM of NAD, in 1.0M ammonia-formate buffer (pH 7.5). Five hundred milligrams of the gel was packed in a column (5 mm i.d. × 70 mm long) and the substrate solution was passed downward through the column at a flow rate of 15.0±0.5 ml/hr. The reaction of leucine production was carried out at 30° C. The maximum conversion ratio was 6.6% and the expressed activity of FDH calculated from the leucine production rate was 69% of the remaining FDH activity in the gel.

What is claimed is:

1. A method for producing an immobilized enzyme, which comprises:
   dispersing an enzyme powder in a water-soluble organic solvent having dissolved therein, in the range of 0.5 to 30% by weight based on the amount of said organic solvent, at least one monomer selected from the group consisting of acrylic esters, methacrylic esters, acrylamide and acrylamide derivatives which are soluble in said organic solvent, said enzyme powder not being dissolved by said organic solvent and remaining dispersed therein;
   polymerizing said at least one monomer in the presence of a cross linking agent and said dispersed enzyme powder, thereby producing a gel matrix in said organic solvent which entraps said dispersed enzyme powder in said gel matrix; and
   displacing said organic solvent with an aqueous solvent, thereby forming gaps in said gel matrix containing said aqueous solvent with said enzyme dissolved therein such that said enzyme is entrapped in said gel matrix.

2. The method according to claim 1, wherein said enzyme powder is made up of purified enzyme or a mixture of microorganism cells and active enzyme.

3. The method according to claim 1, wherein the amount of said enzyme powder to be dispersed is in the range of 5 to 20 parts by weight based on 100 parts by weight of said organic solvent.

4. The method according to claim 1, wherein said organic solvent is selected from the group consisting of acetone, methanol, ethanol, ethylene glycol, formamide, dimethylsulfoxide, methyl cellosolve, N,N-dimethylformamide, dioxane, benzene, cyclohexane, ethyl ether, ethyl acetate, chloroform and halogenated ethylenes.

5. The method according to claim 1, wherein said aqueous solvent is water or an aqueous buffer solution.

6. The method according to claim 1, wherein said acrylic ester is polyethylene glycol diacrylate and 2-hydroxyethyl-acrylate.

7. The method according to claim 1, wherein said methacrylic ester is polyethylene glycol dimethacrylate.

8. The method according to claim 1, wherein said acrylamide derivative is N,N-methylenebisacrylamide.

* * * * *